(12) United States Patent
Aerni et al.

(10) Patent No.: US 9,703,925 B1
(45) Date of Patent: Jul. 11, 2017

(54) RAPID PROCESSING OF BIOLOGICAL SEQUENCE DATA

(71) Applicant: Pivotal Software, Inc., San Francisco, CA (US)

(72) Inventors: Sarah Joann Aerni, San Francisco, CA (US); Mariann Micsinai, Union, NJ (US)

(73) Assignee: Pivotal Software, Inc., San Francisco, CA (US)

( * ) Notice: Subject to any disclaimer, the term of this patent is extended or adjusted under 35 U.S.C. 154(b) by 812 days.

(21) Appl. No.: 14/060,553

(22) Filed: Oct. 22, 2013

(51) Int. Cl.
*G06F 19/00* (2011.01)
*G06F 19/10* (2011.01)

(52) U.S. Cl.
CPC .................................. *G06F 19/10* (2013.01)

(58) Field of Classification Search
CPC .......... G06F 19/22; G06F 19/12; G06F 19/24; G06F 19/28; G06F 19/3431; G06F 17/10; G06F 17/11; G06F 17/2785; G06F 17/30557; G06F 17/30864; G06F 19/16; G06F 19/18; G06F 19/20; G06F 19/345; G06N 3/01
USPC .................................. 702/19, 20; 703/11, 12
See application file for complete search history.

(56) References Cited

U.S. PATENT DOCUMENTS

| | | | |
|---|---|---|---|
| 8,131,472 B2 | 3/2012 | Chow et al. | |
| 8,200,992 B2 * | 6/2012 | Felch | G06F 9/3851 711/100 |
| 8,713,038 B2 * | 4/2014 | Cohen | G06F 17/30463 707/764 |
| 2003/0171876 A1 | 9/2003 | Markowitz et al. | |
| 2004/0117037 A1 * | 6/2004 | Hinshaw | G06F 17/30477 700/2 |
| 2009/0089560 A1 * | 4/2009 | Liu | G06F 9/5066 712/226 |

OTHER PUBLICATIONS

Vijayakumar, S. et al. Proceedings—2012 IEEE 5th International Conference on Cloud Computing CLOUD 2012 pp. 819-827, wherein the conference was held Jun. 24, 2012-Jun. 29, 2012.*
Schmidt et al. Scanning biosequence databases on a hybrid parallel architecture. Euro-Par 2001 Parallel Processing—7th International Euro-Par Conference, Proceedings; Lecture Notes in Computer Science (including subseries Lecture Notes in Artificial Intelligence and Lecture Notes in Bioinformatics) (2001), vol. 2150, pp. 360-370.*

* cited by examiner

*Primary Examiner* — Mary Zeman
(74) *Attorney, Agent, or Firm* — Fish & Richardson P.C.

(57) ABSTRACT

In general, one aspect of the subject matter described in this specification is embodied in operations of processing sequence data by selecting a distribution key according to a type of one or more tasks to be performed on the data. The key is one or more data fields of a sequence data file, e.g., a sequence alignment/map (SAM) format or binary sequence alignment/map (BAM) format file, or derived from one or more data fields of a sequence data file. The sequence data is then distributed to multiple nodes of a parallel processing relational database system. The system performs the tasks of processing the sequence data by executing database queries. The system executes the database queries on multiple nodes in parallel. The system can use query optimization functions built into the database to expedite performance of each task.

24 Claims, 4 Drawing Sheets

RAPID PROCESSING OF BIOLOGICAL SEQUENCE DATA

BACKGROUND

This specification relates to biological sequence data processing.

A sequencing machine can generate sequence data derived from multiple types of biological molecules, including, for example, ribonucleic acid (RNA) and deoxyribonucleic acid (DNA). The biological sequence data is often designated as reads. A single sequencing run can create between thousands and billions of reads. The sequence data, e.g. reads derived from such data sources, can be mapped to a reference genome (e.g. DNA to the reference genome) and stored in files called sequence alignment/map (SAM) files or binary sequence alignment/map (BAM) files, or in any other alternative file format containing the genomic coordinates to which a read may have been mapped or unmapped and additional details, e.g. sequence quality, mate-pair information, or both. Such files frequently reach a size of tens of gigabytes each. Utility programs specialized in processing sequence data, e.g., the Genome Analysis Toolkit (GATK®) or SAMtools® can be used to analyze the SAM or BAM files to identify various patterns in the reads. During processing, these utility programs can sort and index the sequence data, extract particular information from the sequence data, and convert data formats. An individual utility program can execute on a stand-alone computer to perform a processing task. A task of identifying a specific kind of pattern may require sorting, indexing, or converting the data in multiple ways. Even though a specialized utility program can be multi-threaded, each task can last one or more hours due to the amount of data to be processed. In addition, each utility program can easily have a memory footprint of several gigabytes.

SUMMARY

In general, one aspect of the subject matter described in this specification is embodied in operations of processing biological sequence data by selecting a key according to a type of one or more tasks to be performed on the data. The key includes, or is derived from, one or more data fields of the data, for example fields in a SAM or BAM file. The sequence data is then distributed to multiple nodes of a parallel processing relational database system. Distribution of the sequence data is based on the key. For example, the distribution can be based on hashing the key. The parallel processing database system can be a massively parallel processing (MPP) database system. Each node of the MPP database system includes one or more processors and other resources. The parallel processing database system performs the tasks of processing the sequence data by executing database queries. The system executes the database queries on multiple nodes of the MPP database system in parallel. The system can use query optimization functions built into the MPP database to expedite performance of each task.

The use of such parallel processing databases can improve the performance of various analysis tasks in sequence analysis including, for example, identifying sequencing duplicates, identifying highest quality reads or read pairs in these duplicates, identifying motifs in sequences, determining read counts in specific genomic loci on a genome, and identifying allele variants and frequencies. The techniques discussed in this specification allow people to dissect the data in multiple ways, e.g., through rapid querying or manual access, to perform quantitative analysis (e.g., obtaining summary statistics) or qualitative analysis (e.g., observing a feature or identifying a pattern).

The system receives sequence data. As an example, the sequence data includes DNA sequences that have been mapped to a human genome. The mapped DNA sequence data can include reads from one or more sequence data sources, e.g. different samples. Each read includes a representation of a sequence and its mapped location coordinate. The location coordinate indicates a location of a matching, or nearly matching, sequence in a reference sequence. In general, the reference sequence can include a representation of at least a portion of a genetic molecule. The genetic molecule can be a human, animal, plant, viral or bacterial chromosome, fragment, etc. The sequence data can include at least one of DNA sequence data, RNA sequence data, or ChIP sequence data. Other biological sequences can also be used. For example, each of the sequence and the reference sequence can represent a sequence of amino acids in a protein.

The system ingests the mapped sequence data and places the mapped sequence data into a distributed table, referred to as a sequence table. The sequence table is a database table. The database table has a data model of multiple columns and multiple rows. The database table is represented as data records, each data record corresponding to a row of the data model. Each data record represents a read in the sequence data. Each data record has one or more data fields, each data field corresponding to a column in the data model. The data model can have a structure representing fields of a data file having a SAM or BAM format, or another computer-readable or human-readable format, e.g., a browser extensible data (BED) file format.

The system distributes the sequence table to multiple nodes of the parallel processing database based on the distribution key. Each node of the parallel processing database is a computer that receives its portion of the sequence table and stores it locally. Each node is configured to process its portion of the sequence table in parallel to other nodes.

Particular embodiments of the subject matter described in this specification can be implemented to realize one or more advantages. For example, compared to conventional approaches of processing sequence data by a stand-alone computer, processing the sequence data in a parallel processing database can be faster. A system implementing the techniques described in this specification can perform various stages of a task using structured query language (SQL) statements or SQL-like statements, procedures written using an in-database procedural language, or both. By using a query optimizer of an MPP database, the system can make in-database processing of sequence data faster compared to data processing performed by a conventional utility program on a stand-alone computer, e.g., a desktop or laptop computer. For example, the system can perform a genetic analysis task in tens of seconds, whereas a conventional utility program may take hours to perform the same task.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTIONS OF DRAWINGS

Like reference numbers and designations in the various drawings indicate like elements.

DETAILED DESCRIPTION

Figure 1:
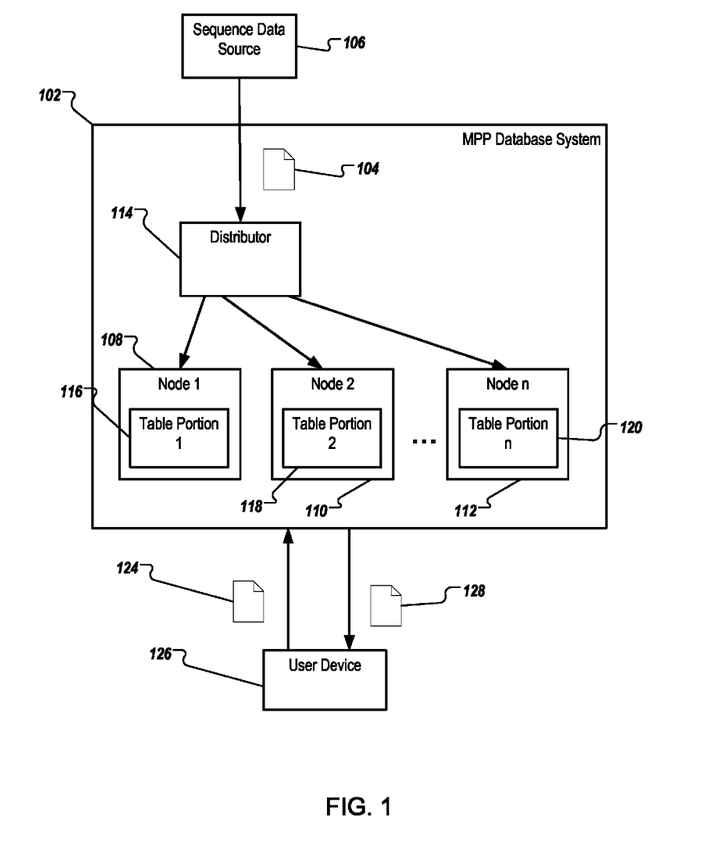
FIG. 1 is a block diagram of an example system implementing in-database parallel processing of sequence data.

FIG. 1 is a block diagram of an example system implementing in-database parallel processing of sequence data. The system includes a parallel processing database system 102. The system processes sequence data 104 in the parallel processing database system 102.

The system receives the sequence data 104 originating from a sequence data source 106. The sequence data 104 can be received in the form one or more SAM files, BAM files, or files in another format. The sequence data source 106 can include a genetic sequencing machine or a sequence alignment system. The sequence data source 106 can be a distributed file storage system. The sequence data 104 can include multiple files distributed in the file storage system. The sequence data 104 can include raw reads or mapped reads. The sequence alignment system can include a computer programmed to execute sequence alignment software, e.g., a Burrows-Wheeler aligner. The sequence data 104 can include a large number of reads from genetic material. Each read includes a representation of a sequence of nucleotide bases in the genetic material. Once mapped, each read includes a representation of a location, e.g., a coordinate of the sequence of bases in a reference sequence. A read can be a multi-segment read including paired reads obtained from the ends of fragments. The multi-segment read can include representations of multiple sequences representing a different sequence of nucleotide bases, e.g., each read in the pair (mate-pairs), and multiple locations each corresponding to one of the sequences. Mate-pairs are most frequently represented in a file with a single line per pair, but with information about the mate-pair also present in a field.

The parallel processing database system 102 is an MPP database system having multiple independent nodes. For example, the parallel processing database system 102 can be a shared-nothing MPP database system. Some examples of parallel processing databases are the Pivotal Greenplum Database®. Each node of the parallel processing database system 102 includes one or more processors, one or more associated storage devices, e.g., memory and disk, and one or more networking devices. The parallel processing database system 102 divides the processing of data between the nodes. The nodes each process a portion of the data in parallel to other nodes. In the example shown, upon receiving the sequence data 104, the system distributes the sequence data 104 to multiple nodes of the parallel processing database system 102, each node receiving and storing a non-overlapping portion of the sequence data 104.

For example, the parallel processing database system 102 illustrated in FIG. 1 includes n nodes including a first node 108, a second node 110, through an n-th node 112. A distributor 114 transmits the sequence data 104 to the nodes to be stored, one node for each data item. The distributor 114 can be a hardware or software component of the parallel processing database system 102 configured to perform hashing functions on the sequence data 104.

The distributor 114 distributes the sequence data 104 to the nodes according to a distribution key or a set of distribution keys. The distribution key can be a data field of the sequence data 104, e.g., a location data field, or a composite of multiple fields of the sequence data 104, e.g., multiple location data fields from a paired sequence.

The system performs tasks that are conventionally performed by application programs, in the genetic sequencing example on BAM or SAM files, by executing database queries. For example, the system receives a query 124 from a user device 126, and executes the query 124 in the parallel processing database system 102. The query 124 can be a relational database query, e.g., an SQL query including a "SELECT" statement. The user device 126 can be a device, e.g., a desktop or laptop computer, a tablet, or a smartphone, coupled to the parallel processing database system 102 through a communications network. The system provides query results 128 to the user device 126.

In an example application of the techniques described, the system performs a task of identifying sequencing duplicates created during DNA sequencing. The system in the example uses a paired-sequencing approach in which two sequences are read from the ends of a DNA fragment. For each sequence in the pair, the system defines the location coordinate of one pair, and information about the other, "mate-pair" as. The system parses a SAM or BAM file of multiple reads, and stores result of the parse in a sequence table in the parallel processing database system 102. An example sequence table is provided below in Table 1.

TABLE 1

| pairID text | matePair int | chrom int | locus bigint | mapq int |
| --- | --- | --- | --- | --- |
| SRR1.1 | 1 | 1 | 120345 | 42 |
| SRR1.1 | 2 | 1 | 140535 | 43 |
| SRR1.2 | 1 | 1 | 120345 | 28 |
| SRR1.2 | 2 | 1 | 140535 | 23 |
| SRR1.543 | 1 | 1 | 140535 | 40 |
| SRR1.543 | 2 | 1 | 120345 | 37 |

The sequence table is divided into portions 116, 118, and 120 based on distribution key "pairID." In this simplified sample table, the pairID is an identifier for the sequence pair so that each pair has the same ID. The pairID may also include a sequence run identifier, in this case, "SRR1," to allow multiple runs to be stored in the same sequence table. The field "matePair" stores a unique identifier for the particular read in the pair. The field "chrom" stores a mapped chromosome for the read. The field "locus" stores the mapped base location on the chromosome for that read. The field "Mapq" stores a quality of the mapping of the reads, for example, a raw or scaled probability determined by another mapping algorithm, e.g., Phred. In this particular example, the value provided in the "mapq" field is unique to each read in a pair. The sum of the two "mapq" scores gives a score of the pair. The system executes a SQL query to identify duplicates in the sequence table stored in the parallel processing database system 102. Example code for the identification of duplicates using a SQL query is shown below in Table 2.

TABLE 2

SELECT compoundKey, count(*) FROM( SELECT CASE WHEN
pair1.locus<pair2.locus
　　THEN
　　　　pair1.chrom||'.'||pair1.locus||'.'||pair2.chrom||'.'||pair2.locus
　　ELSE
　　　　pair2.chrom||'.'||pair2.locus||'.'||pair1.chrom||'.'||pair1.locus TABLE 2-continued

```
        END compoundKey
    FROM
        ( SELECT * FROM read_table WHERE matePair=1)pair1
        JOIN
        ( SELECT * FROM read_table WHERE matePair=2)pair2
        USING(pairID)
    ) AS getPairs
    GROUP BY compoundKey;
```

By executing the query in Table 2, the system identifies loci where multiple reads are mapping. This can be used for filtering out pairs and keeping only the top scoring pair. In the example application of the techniques described, the system performs a task of identifying groups of reads that map to the same genomic coordinates. The above example described paired-end sequence data. The system can identify groups of reads that map to the same genomic coordinates using single reads, or any other duplicated sequences obtained from a sample.

In an example application of the techniques described, the system performs a task of identifying the highest quality pairs of reads or highest quality single reads. The system can identify the highest quality pair of reads or highest quality single reads by counting number of pairs or single reads that map to a same region on a genome as described in Table 2. The system can then identify the top-scoring pair. Example code for identifying the top scoring pair using a SQL query is shown below in Table 3.

TABLE 3

```
CREATE TEMP TABLE seqpairs AS(
    SELECT CASE WHEN pair1.locus<pair2.locus
        THEN
            pair1.chrom||'.'||pair1.locus||'.'||pair2.chrom||'.'||pair2.locus
        ELSE
            pair2.chrom||'.'||pair2.locus||'.'||pair1.chrom||'.'||pair1.locus
        END compoundKey,
        pair1.pairID,
        pair1.mapq+pair2.mapq mapq
    FROM
        ( SELECT * FROM read_table WHERE matePair=1) pair1
        JOIN
        ( SELECT * FROM read_table WHERE matePair=2) pair2
        USING(pairID)
) DISTRIBUTED BY(compoundKey);
CREATE TEMP TABLE mapcounts AS(
    SELECT compoundKey, count(*)
    FROM seqpairs
    GROUP BY 1
)DISTRIBUTED BY (compoundKey);
SELECT pairID
FROM (
    SELECT pairID,
    ROW_NUMBER( )
        OVER (PARTITION BY compoundKey ORDER BY
        mapq DESC)
    FROM seqpairs
    JOIN
    (SELECT * FROM mapcounts WHERE COUNT>1)MAPS
    USING(compoundKey)
)
WHERE row_number=1
UNION ALL
SELECT pairID
FROM seqpairs
JOIN
    (SELECT * FROM mapcounts WHERE COUNT=1) MAPS
    USING(compoundKey)
```

The final result of the query in Table 3 generates the list of pairIDs that are (1) uniquely mapped read pairs or (2) the top-scoring map quality pair for a set of duplicates.

Figure 2:
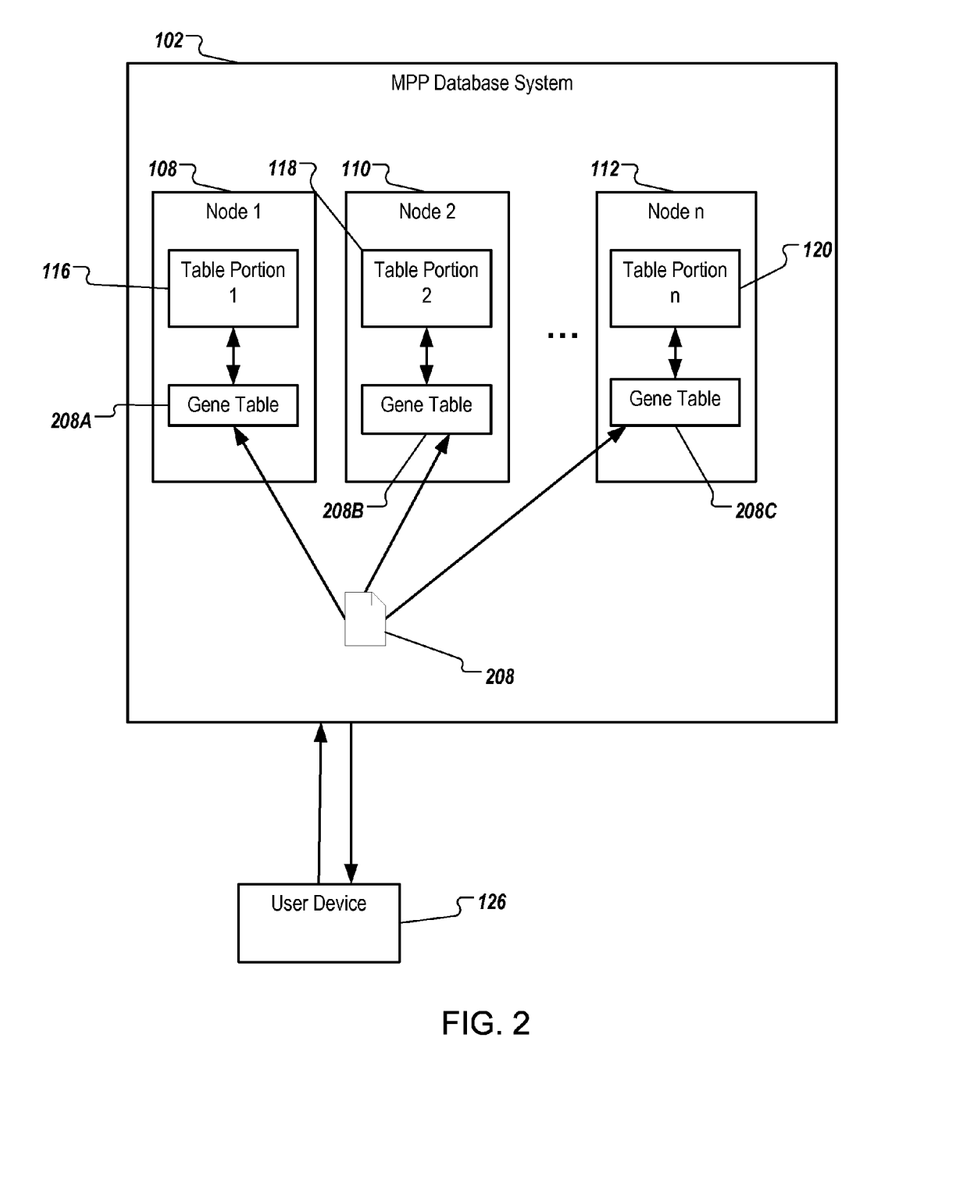
FIG. 2 is a block diagram of an example system for determining a read count of a feature in a genome.

FIG. 2 is a block diagram illustrating an example system for determining a read count of a feature in a genome. The system can perform various tasks that involve counting features by performing table joins. The features can refer to any arbitrarily defined region.

For example, the task can include determining a count of how many reads in a sample of sequence data are mapped to one or more region features. The region features can include exons for gene expression measures or binding sites of a biomolecule or ion. The task can include determining a count of how many chromatin immunoprecipitation sequencing (ChIP-seq) reads are mapping to a region. Conventionally, these tasks can be performed by various application programs manipulating SAM or BAM files. The system illustrated in FIG. 2 performs these tasks by performing table joins in parallel processing database system 102.

In some implementations, the system can copy one or more gene tables 208 to each of the first node 108, the second node 110, through the n-th node 112 of the parallel processing database system 102. Each gene table 208 is a table of a relational database storing information of one or more particular genomes.

Each of the first node 108, the second node 110, through the n-th node 112 stores a local copy, e.g., gene tables 208A, 208B, and 208C of the gene table 208. An example gene table 208 is provided below in Table 4.

TABLE 4

| geneID<br>text | featureID<br>text | chrom<br>int | startLoc<br>bigint | stopLoc<br>bigint |
|---|---|---|---|---|
| A | Exon1 | 1 | 123456 | 123556 |
| A | Exon2 | 1 | 123856 | 124156 |

In this simplified sample table for genetic sequences, the field "geneID" stores a unique gene identifier. The field "featureID" stores a particular component of that gene, e.g. "exon 1." The fields "chrom," "startLoc," and "stopLoc" give the physical location of the feature identified by the featureID in a genome, e.g., a human genome. These fields, individually or in combination, can be used to determine if a particular read maps within the feature.

The system determines a count for sequences in the same region by performing a table join in the parallel processing database system 102. For example, with RNA sequence data, the system can execute a read count query joining a sequence table ("read_table") of the RNA sequence data and the gene table 208 having an example name "gene_table" in one or more nodes of parallel processing database system 102. The gene table specifies a start location ("startLoc") and an end location ("stopLoc") for each region corresponding to the feature. Example SQL code for the read count query is listed below in Table 5. In the example of Table 5, the read lengths are provided to be 50 base pairs. In various implementations, the read length can be determined in various ways. For example, the read length can be obtained from the data directly. An end location of a mapped read may also be directly included as a field in the mapped reads table. For simplicity, no insertions or deletions in the mappings are provided in the example shown. However, insertions or deletions can be accounted for in various implementations. In addition, in the example shown, orientation of the mapped reads is already accounted for and does not need to be represented in the query. In an implementation that considers orientation, the orientation can be represented in an extra data field.

TABLE 5

```
SELECT geneID, count (*)
FROM read table JOIN gene_table
ON      (gene_table.chrom = read_table.chrom) AND
        (gene_table.startLoc <= read_table.loc+50) AND
        (gene_table.endLoc >= read_table.loc)
GROUP BY gene_table.id
```

The system can perform a task of identifying allele variants and determining frequencies of the variants at each locus of a genome. The system performs the task by executing an allele counting query in the parallel processing database system 102. Example code for the allele counting SQL query is shown below in Table 6. More sophisticated statistics may also be obtained by extending this concept to include other fields, for example mapping quality or base calling quality. Again, for simplicity, assumptions for the example are that there are no insertions or deletions in the mapping and that orientation of the read has already been accounted for in the data.

TABLE 6

```
SELECT nucleotidePos,nucleotide,count(*)
FROM(
  SELECT *,substr(seq,ind,1) nucleotide, pos+ind-1 nucleotidePos
  FROM(
  SELECT seq,qual,pos,generate_series(1,length(seq)) ind
  FROM read_table
  )reads
)singleNucs
GROUP by 1,2
```

Figure 3:
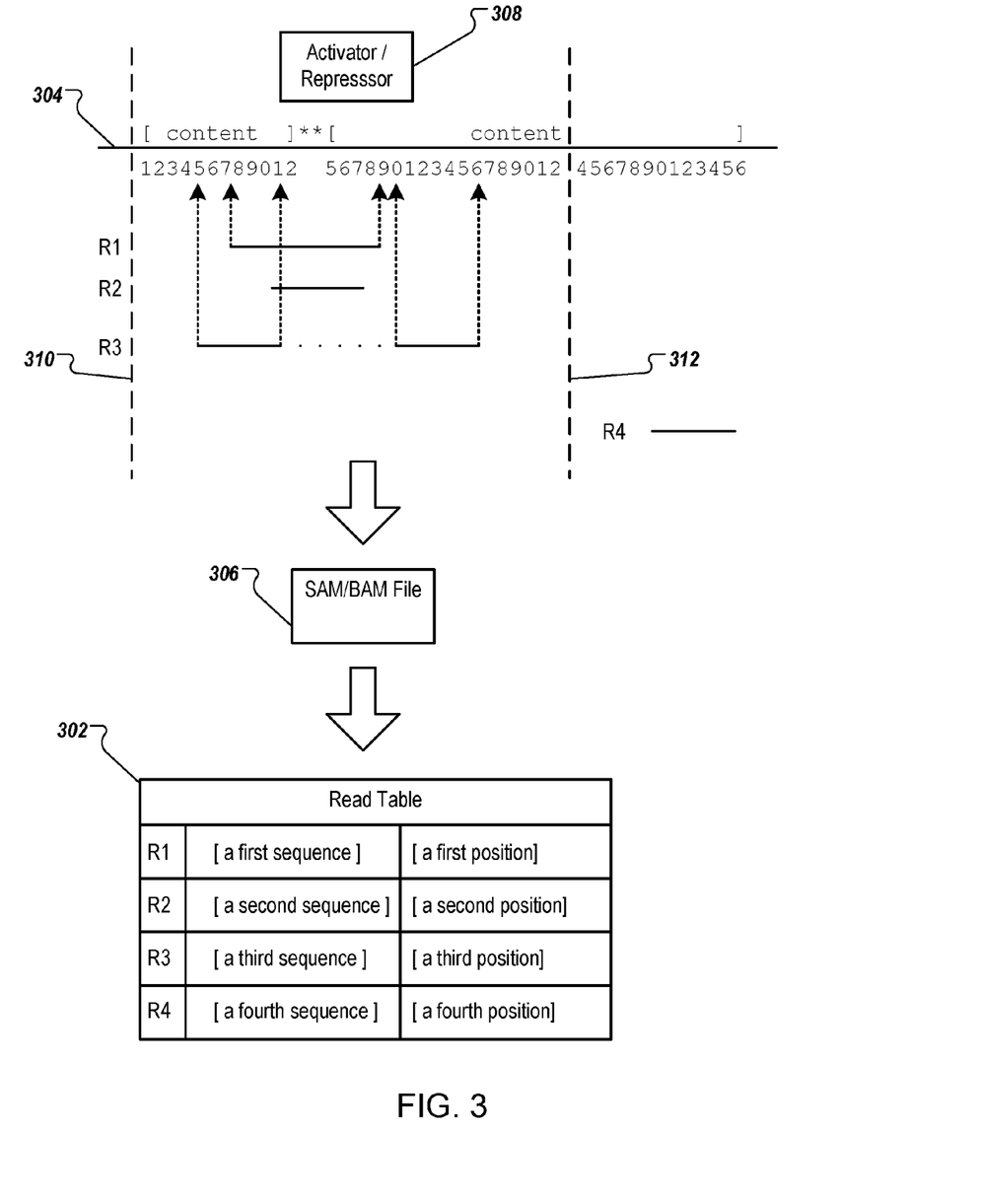
FIG. 3 is a block diagram illustrating structure of an example sequence table showing a subset of fields.

FIG. 3 is a block diagram illustrating structure of an example sequence table 302 showing a subset of fields. In the example shown, sequence table 302 is configured to store DNA sequence read data.

Example DNA sequence read data include four reads, R1, R2, R3, and R4. Each read includes a representation of bases matching a section of a reference sequence 304. The reference sequence 304 can be a genetic molecule or a section of a genetic molecule having multiple bases, commonly represented by the letters A, T, G, and C. Each read has a reference location, which includes a chromosome identifier and a distance, in bases, from a beginning of the reference sequence. For example, read R1 includes a match starting at location 100008 and ending at location 100018. Read R3 includes a match of two segments. A first segment of the match has a first start location at 100005 and a first end location 100010. A second segment has a start location at 100020 and an end location 100026.

Reads R1, R2, R3, and R4 may have been obtained from a SAM file 306. A system implementing in-database parallel processing of ChIP sequence data parses the SAM file 306 and populates the sequence table 302. The sequence table 302 has multiple columns corresponding to identifiers of the reads, the sequence of each read, and locations of the match of the sequences in the reference. The sequence table 302 has multiple rows, each corresponding to an individual read.

To determining a degree of activeness of an activator or repressor 308, a user can use the system to determine a count of reads in a region proximate to a section of the reference sequence 304 that binds with the activator or repressor 308. The region can be defined by a start location 310 (e.g., "100000") and an end location 312 (e.g., "100033") on chromosome <number> (e.g., 1). The system can determine the read count in response to a query on the sequence table 302 using the start location 310 and the end location 312 as selection criteria. In this example, the read count is three (including R1, R2, and R3), similarly to prior read counting for genomic feature. In various implementations, a read count can be performed in windows having various sizes. For example, a read count can be performed on various length scales, e.g., for one nucleotide, or on X kilobytes of data. The read count may be specified for an exact genomic location. Example code for the counting reads from ChIP-seq experiment SQL query is shown below in Table 7.

TABLE 7

```
SELECT count(*)
  FROM read_table
  WHERE chrom = 1 AND (100000<= lo) AND (100033>
  loc+50)
```

Figure 4:
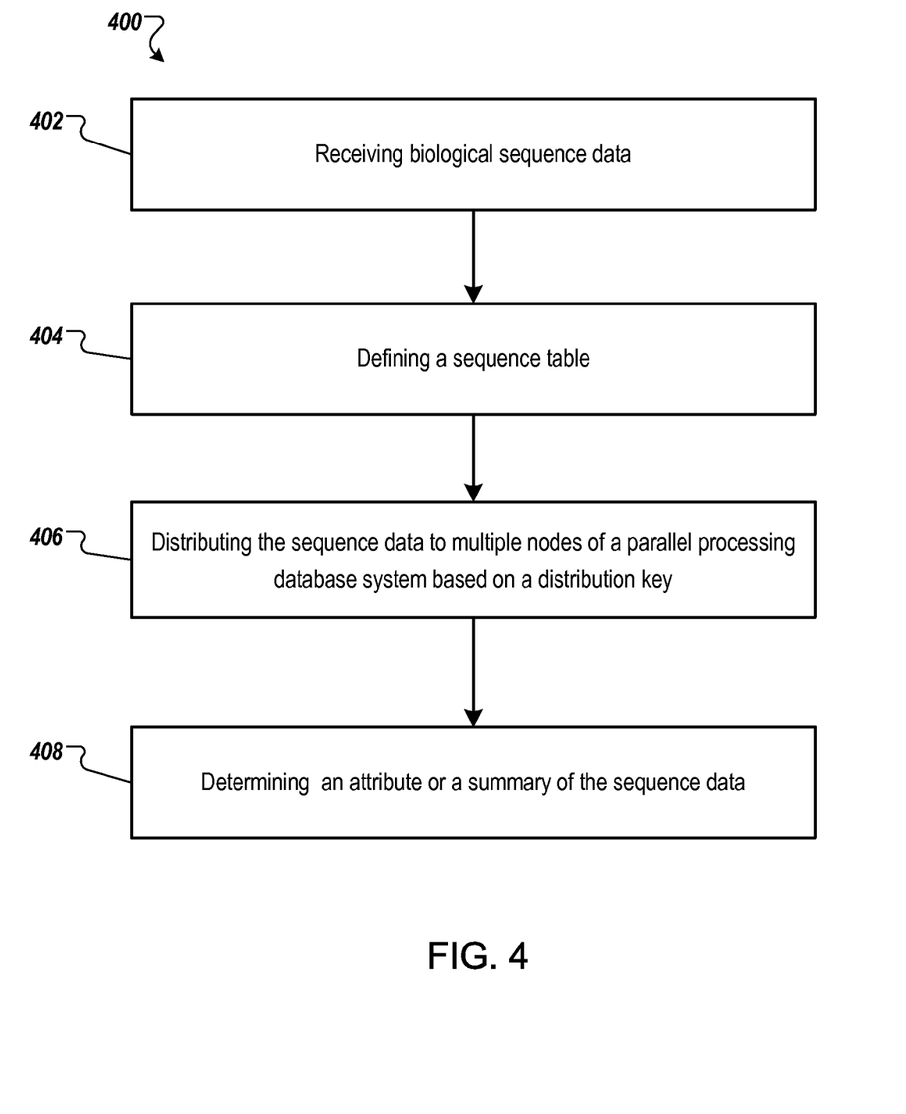
FIG. 4 is a flowchart illustrating an example method of in-database parallel processing of sequence data.

FIG. 4 is a flowchart illustrating an example method 400 of in-database parallel processing of sequence data. The method 400 can be performed by the parallel processing database system 102 described above in reference to FIGS. 1-3. By performing the method 400, the system can accomplish various bioinformatics analysis tasks including, for example, identifying sequencing duplicates, identifying highest quality reads or read pairs in duplicates, determining read counts on features in a genome, and identifying allele variants and frequencies.

The system receives (402) sequence data. The sequence data, e.g., sequence data 104 of FIG. 1, includes reads from one or more sequence data sources.

The system defines (404) a sequence table. The sequence table, e.g., sequence table 302 of FIG. 3, is a database table. The database table has a sequence data field, and a location data field. In some implementations, the database table also includes an identifier data field. The database table can include additional fields for storing an end location of a mapping and other information.

The system distributes (406) the sequence data to multiple nodes of the system based on the distribution key. The system parses the sequence data, for example RNA sequences to generate a data record for each read. The data record has an identifier data field storing an identifier of the read. The data record has a sequence data field storing a representation of the RNA sequence of the read. The data record has a location data field storing a representation of the location coordinate of the read. The data record also includes a field storing a representation of the chromosome to which the read is mapped. It may also contain additional fields including mapping quality, orientation of the mapped read, base quality scores and in the case of paired-end sequencing information about the other pair. The system identifies node for storing the data record based on the distribution key and content stored in one or more data fields of the data record that correspond to the one or more data fields of the distribution key. For example, the system can distribute the data records based on location or a combination of location and chromosome. The system then stores the data record in a sequence table of the identified node.

To distribute the sequence data to the nodes, the system can hash the distribution key or keys. In some implementations, the system can perform a procedure that includes determining multiple value ranges of the distribution key based on a node count, e.g., number of nodes, of the parallel processing database system. Each different value range corresponds to a different node of the parallel processing database system. The system identifies the node for storing the data record based on a match between the value range corresponding to the node and the content stored in the one or more data fields of the data record. The distribution key can be a composite key having a first sequence associated with a corresponding first location and a second sequence associated with a second location. An example was given earlier, in Table 3, where the composite key included the combined chromosome and loci of each of the reads in a pair, with the information of the read with the smaller locus coming first. The composite key can be stored in a new data field.

The system determines (408) an attribute or a summary of the sequence data using a same database query executed on each of the nodes of the parallel processing database system. The attribute or summary of the sequence data can include at least one of an average value, a maximum value, a minimum value in the sequence data. The average, maximum, or minimum value can each be determined based on one or more attributes of the mapped read, e.g., quality. The attribute or summary can include a count of number of sequences obtained or sampled from a source (e.g. number of reads in a gene). The attribute or summary can include an assessment of the distribution of variable values observed at a particular location in the sequence (e.g. a mutation). The attribute or summary can include one or more quality assessments of the sequence data, for example, a distribution of insert size for pairs or Phred scores of the reads. The attribute or summary can include a feature of interest, e.g., a feature of the sequence or location, for visual inspection of sequences.

In some implementations, determining the attribute or summary includes determining a read count in a region of the reference sequence. The read count can include a number of pairs of reads that map to the region or a number of single reads that map to the region. The system identifies duplicate reads based on the number of pairs of reads that map to the specific location or the number of single reads that map to the specific location.

Each node of the system stores a gene table. The gene table stores data on a genetic feature in the region. The gene table can store the reference sequence. The read count is a read count on the genetic feature. To determine the read count, the system perform table join between the sequence table and the gene table. The system performs the table join in parallel on multiple nodes. The system can then determine the read count on a feature by performing a count on a group of reads in the sequence table corresponding to the feature as defined in the gene table. The count is performed in parallel by multiple nodes. The system can provide results of the read count to a user, e.g., by presenting the read count on a display device or saving the read count in a file on a storage device.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory program carrier for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example a programmable processor, a computer, or multiple processors or computers. The apparatus can also be or further include special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communications network. Examples of communications networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

What is claimed is:

1. A method, comprising:
    receiving sequence data, the sequence data comprising reads from one or more sequence data sources, each read including a sequence and a location coordinate, the location coordinate indicating a location of the sequence on a reference sequence;
    defining a sequence table, the sequence table being a database table having a sequence data field and a location data field;
    distributing the sequence data to a plurality of nodes of a parallel processing database system based on a distribution key, each node of the parallel processing database system comprising a processor configured to process a portion of the sequence table stored on the node locally to the processor and in parallel to other nodes, the distribution key comprising one or more data fields of the sequence table, wherein distributing the sequence data comprises:
        generating a data record for each read, a sequence data field of the data record storing a representation of the sequence of the read, and a location data field of the data record storing a representation of the location coordinate of the read;
        identifying a node for storing the data record based on the distribution key and content stored in one or more data fields of the data record that correspond to the one or more data fields of the distribution key; and
        storing the data record in a sequence table of the identified node; and
    executing a same database query on each of the nodes of the parallel processing database system, the database query operable to retrieve an attribute or summary of the sequence data.

2. The method of claim 1, wherein:
    the reference sequence includes a representation of at least a portion of a genome or genetic sequence,
    the sequence data comprise at least one of deoxyribonucleic acid (DNA) sequence data, ribonucleic acid (RNA) sequence data, or chromatin immunoprecipitation (ChIP) sequence data, and
    the database table has a structure representing fields of a data file having a sequence alignment/map (SAM), binary sequence alignment/map (BAM), or browser extensible data (BED) format.

3. The method of claim 1, wherein the distribution key comprises a composite key having a first sequence associated with a corresponding first location and a second sequence associated with a second location.

4. The method of claim 1, wherein:
the attribute or summary of the sequence data comprises at least one of an average value, a maximum value, a minimum value among multiple rows of a same data field in the sequence data.

5. The method of claim 1, wherein:
the database query comprises a join operator for joining two database tables.

6. The method of claim 1, wherein:
the attribute or summary comprises a read count, the read count being a number of pairs of reads or a number of single reads that map to a region; and
the method comprises identifying duplicate reads based on the number of pairs of reads or the number of single reads that map to the region.

7. The method of claim 1, wherein determining the attribute or summary of the sequence data comprises determining a read count in a region of the reference sequence, the region being defined by a plurality of locations or a single location, the database query having a grouping clause corresponding to the region.

8. The method of claim 7, wherein the read count is a read count on a genetic feature, and
determining the read count comprises performing a table join between the sequence table and the gene table, the table join being performed in parallel on the nodes.

9. A non-transitory storage device storing instructions operable to cause one or more computers to perform operations comprising:
receiving sequence data, the sequence data comprising reads from one or more sequence data sources, each read including a sequence and a location coordinate, the location coordinate indicating a location of the sequence on a reference sequence;
defining a sequence table, the sequence table being a database table having a sequence data field and a location data field;
distributing the sequence data to a plurality of nodes of a parallel processing database system based on a distribution key, each node of the parallel processing database system comprising a processor configured to process a portion of the sequence table stored on the node locally to the processor and in parallel to other nodes, the distribution key comprising one or more data fields of the sequence table, wherein distributing the sequence data comprises:
generating a data record for each read, a sequence data field of the data record storing a representation of the sequence of the read, and a location data field of the data record storing a representation of the location coordinate of the read;
identifying a node for storing the data record based on the distribution key and content stored in one or more data fields of the data record that correspond to the one or more data fields of the distribution key; and
storing the data record in a sequence table of the identified node; and
executing a same database query on each of the nodes of the parallel processing database system, the database query operable to retrieve an attribute or summary of the sequence data.

10. The non-transitory storage device of claim 9, wherein:
the reference sequence includes a representation of at least a portion of a genome or a genetic sequence,
the sequence data comprise at least one of deoxyribonucleic acid (DNA) sequence data, ribonucleic acid (RNA) sequence data, or chromatin immunoprecipitation (ChIP) sequence data, and
the database table has a structure representing fields of a data file having a sequence alignment/map (SAM), binary sequence alignment/map (BAM), or browser extensible data (BED) format.

11. The non-transitory storage device of claim 9, wherein the distribution key comprises a composite key having a first sequence associated with a corresponding first location and a second sequence associated with a second location.

12. The non-transitory storage device of claim 9, wherein:
the attribute or summary of the sequence data comprises at least one of an average value, a maximum value, a minimum value among multiple rows of a same data field in the sequence data.

13. The non-transitory storage device of claim 9, wherein the database query comprises a join operator for joining two database tables.

14. The non-transitory storage device of claim 9, wherein:
the attribute or summary comprises a read count, the read count being a number of pairs of reads or a number of single reads that map to a region; and
the method comprises identifying duplicate reads based on the number of pairs of reads or the number of single reads that map to the region.

15. The non-transitory storage device of claim 9, wherein determining the attribute or summary of the sequence data comprises determining a read count in a region of the reference sequence, the region being defined by a plurality of locations or a single location, the database query having a grouping clause corresponding to the region.

16. The non-transitory storage device of claim 15, wherein the read count is a read count on a genetic feature, and
determining the read count comprises performing a table join between the sequence table and the gene table, the table join being performed in parallel on the nodes.

17. A system comprising:
a plurality of nodes of a parallel processing database system, each node of the parallel processing database system comprising a processor; and
a non-transitory storage device storing instructions operable to cause the nodes to perform operations comprising:
receiving sequence data, the sequence data comprising reads from one or more sequence data sources, each read including a sequence and a location coordinate, the location coordinate indicating a location of the sequence on a reference sequence;
defining a sequence table, the sequence table being a database table having a sequence data field and a location data field;
distributing the sequence data to a the nodes based on a distribution key, each node configured to process a portion of the sequence table stored on the node locally to the node and in parallel to other nodes, the distribution key comprising one or more data fields of the sequence table, wherein distributing the sequence data comprises:
generating a data record for each read, a sequence data field of the data record storing a representation of the sequence of the read, and a location data field of the data record storing a representation of the location coordinate of the read;
identifying a node for storing the data record based on the distribution key and content stored in one or more data fields of the data record that correspond to the one or more data fields of the distribution key; and storing the data record in a sequence table of the identified node; and executing a same database query on each of the nodes of the parallel processing database system, the database query operable to retrieve an attribute or summary of the sequence data.

18. The system of claim 17, wherein:

the reference sequence includes a representation of at least a portion of a genome or a genetic sequence, the sequence data comprise at least one of deoxyribonucleic acid (DNA) sequence data, ribonucleic acid (RNA) sequence data, or chromatin immunoprecipitation (ChIP) sequence data, and the database table has a structure representing fields of a data file having a sequence alignment/map (SAM) or binary sequence alignment/map (BAM) format.

19. The system of claim 17, wherein the distribution key comprises a composite key having a first sequence associated with a corresponding first location and a second sequence associated with a second location.

20. The system of claim 17, wherein:

the attribute or summary of the sequence data comprises at least one of an average value, a maximum value, a minimum value among multiple rows of a same data field in the sequence data.

21. The system of claim 17, the database query comprising a join operator for joining two database tables.

22. The system of claim 17, wherein:

the attribute or summary comprises a read count, the read count being a number of pairs of reads or a number of single reads that map to a region; and the method comprises identifying duplicate reads based on the number of pairs of reads or the number of single reads that map to the region.

23. The system of claim 17, wherein determining the attribute or summary of the sequence data comprises determining a read count in a region of the reference sequence, the region being defined by a plurality of locations or a single location, the database query having a grouping clause corresponding to the region.

24. The system of claim 23, wherein the read count is a read count on a genetic feature, and determining the read count comprises performing a table join between the sequence table and the gene table, the table join being performed in parallel on the nodes.

* * * * *

UNITED STATES PATENT AND TRADEMARK OFFICE
CERTIFICATE OF CORRECTION

PATENT NO. : 9,703,925 B1  
APPLICATION NO. : 14/060553  
DATED : July 11, 2017  
INVENTOR(S) : Sarah Joann Aerni et al.

Page 1 of 1

It is certified that error appears in the above-identified patent and that said Letters Patent is hereby corrected as shown below:

In the Claims

Column 14, Line 54, in Claim 17: delete "a the" and insert --the--, therefor.

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*